United States Patent
Sun

(10) Patent No.: US 10,246,540 B2
(45) Date of Patent: Apr. 2, 2019

(54) RAPID AZEOTROPIC PHOTO-COPOLYMERIZATION OF STYRENE AND METHACRYLATE DERIVATIVES AND USES THEREOF

(71) Applicant: ADA Foundation, Chicago, IL (US)

(72) Inventor: Jirun Sun, Rockville, MD (US)

(73) Assignee: ADA FOUNDATION, Chicago, IL (US)

( * ) Notice: Subject to any disclaimer, the term of this patent is extended or adjusted under 35 U.S.C. 154(b) by 44 days.

(21) Appl. No.: 15/276,821

(22) Filed: Sep. 27, 2016

(65) Prior Publication Data

US 2017/0088656 A1    Mar. 30, 2017

Related U.S. Application Data

(60) Provisional application No. 62/234,088, filed on Sep. 29, 2015.

(51) Int. Cl.
| | | |
|---|---|---|
| *C08F 220/68* | (2006.01) | |
| *A61K 6/00* | (2006.01) | |
| *C09D 11/107* | (2014.01) | |
| *B33Y 70/00* | (2015.01) | |
| *A61K 6/083* | (2006.01) | |

(Continued)

(52) U.S. Cl.
CPC .......... *C08F 220/68* (2013.01); *A61K 6/0023* (2013.01); *A61K 6/0052* (2013.01); *A61K 6/083* (2013.01); *B33Y 70/00* (2014.12); *C08F 216/125* (2013.01); *C08F 222/1006* (2013.01); *C08K 3/36* (2013.01); *C09D 11/101* (2013.01); *C09D 11/107* (2013.01);

(Continued)

(58) Field of Classification Search
CPC ............. C08F 220/68; C08F 222/1006; C08F 216/125; C09D 129/10; C09D 11/109; C09D 133/14; C09J 133/14; C09J 129/10; C08K 3/36; A61K 6/0023; A61K 6/0052; A61K 6/083; B33Y 70/00
See application file for complete search history.

(56) References Cited

U.S. PATENT DOCUMENTS 5,980,790 A * 11/1999 Kuwahara ............. C08F 220/14
264/101
2003/0134925 A1 * 7/2003 Guzauskas ............. A61K 6/083
522/71

(Continued)

OTHER PUBLICATIONS

Sun et al. "Preparation of Dental Resins Resistant to Enzymatic and Hydrolytic Degradation in Oral Environments", Biomacromolecules, 16, 3381-3388 (Year: 2015).*

(Continued)

*Primary Examiner* — Mark Eashoo
*Assistant Examiner* — Jessica M Roswell
(74) *Attorney, Agent, or Firm* — Key IP Law Group, PLLC

(57) ABSTRACT

A composition of matter includes a mixture of styrene derivative monomers and methacrylate/acrylate derivative monomers, which have one or more urethane, carbamate, amide, and/or amine functional groups, and initiators, and the compositions are used to achieve composition control of the forming polymer, with the mole fraction of acrylate/methacrylate and styrene moieties in the forming polymer determined preferably by the chemistry and composition of the feeding monomers rather than the viscosity of the monomers.

18 Claims, 1 Drawing Sheet

(51) Int. Cl.
*C08F 216/12* (2006.01)
*C08K 3/36* (2006.01)
*C09D 129/10* (2006.01)
*C09D 133/14* (2006.01)
*C09J 129/10* (2006.01)
*C09J 133/14* (2006.01)
*C08F 222/10* (2006.01)
*C09D 11/101* (2014.01)

(52) U.S. Cl.
CPC ......... *C09D 129/10* (2013.01); *C09D 133/14* (2013.01); *C09J 129/10* (2013.01); *C09J 133/14* (2013.01)

(56) References Cited

U.S. PATENT DOCUMENTS

2011/0166306 A1* 7/2011 Stansbury ............ A61K 6/0017
526/205
2015/0257986 A1* 9/2015 Sun et al. ............ A61K 6/0835
522/115

OTHER PUBLICATIONS

Jia et al. "Crown Ether Cavity-Containing Copolymers via Controlled Alternating Cyclocopolymerization", Macromolecules, 44, 6311-6317 (Year: 2011).*

* cited by examiner

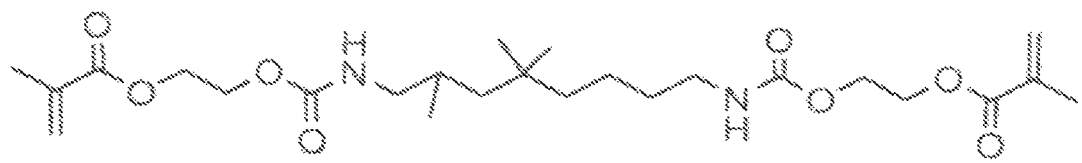
FIG. 1A
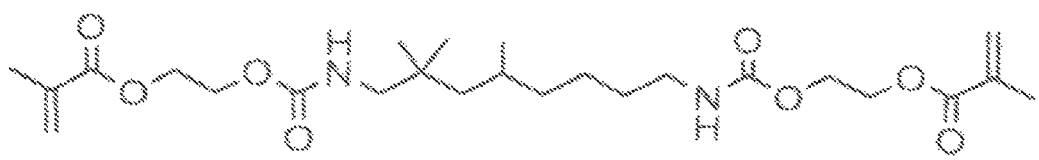
FIG. 1B
FIG. 2
UDMA + TEG-DVBE + PHOTO-INITIATOR + LIGHT IRRADIATION → RESIN
FIG. 3

RAPID AZEOTROPIC PHOTO-COPOLYMERIZATION OF STYRENE AND METHACRYLATE DERIVATIVES AND USES THEREOF

RELATED APPLICATIONS

This application claims the benefit of provisional patent application 62/234,088 filed Sep. 29, 2015 and entitled RAPID AZEOTROPIC PHOTO-COPOLYMERIZATION OF STYRENE AND METHACRYALATE DERIVATIVES FOR DENTAL APPLICATIONS, the disclosure of which is hereby incorporated by reference.

BACKGROUND

Photo-polymerization is a process in which a monomer is converted to a polymer; the process is initiated by the absorption of visible or ultraviolet light. The light may be absorbed either directly by the reactant monomer (direct photo-polymerization) or by a photosensitizer that absorbs the light and then transfers energy to the monomer. The monomers then form a long chain or crosslinked network.

Some current dental restorative compositions rely on photo-copolymerization of resin monomers to form a stable, solid mass in an oral environment. However, to be practically useful, the polymerization must occur in a relatively short time frame. This need for rapid polymerization precludes the use of many materials and compositions that could perform well in an oral environment. As an example, styrene derivatives may perform satisfactorily in an oral environment but current styrene derivative compositions require many tens of minutes or hours to polymerize, making such compositions unsuitable for dental restorative applications. Furthermore, current methacrylate derivative-based compositions, and their accompanying use instructions, may not produce satisfactory durability and esthetics over time. In addition to a short average service life, these compositions are subject to leaching of unreacted monomers and system degradation by hydrolysis of acid, base, or enzymes.

In addition, although the polymerization rate of styrene may be improved through copolymerization with methacrylate monomers, the resulting composition may experience a significant composition shift as the conversion of monomers increases. Vinyl ether resins (VER) as an example, are copolymers of styrene and dimethacrylate monomers. At a high monomer conversion, more styrene is converted into polymer due to diffusion limitations. The dimethacrylate monomers are more viscous than styrene, and thus diffuse more slowly than styrene to reach radicals as the polymerization progresses. This diffusion limitation becomes more obvious for VERs when styrene derivatives have two double bonds on a single monomer. The composition shift of copolymers at different monomer conversions may generate inconsistent physical and mechanical properties in the resulting polymers.

SUMMARY

Disclosed are compositions for enzymatically and hydrolytically stable dental applications, and methods for producing such compositions that can yield highly cross-linked, strong and durable polymers that form rapidly when exposed to light. The compositions may be used in restorative dentistry and can withstand the challenging conditions of the oral environment; however, the compositions may be useful in additional applications such as in medical devices, as coating and packing materials, as adhesives, as filters, and in 3D printing. The composition is used to make thermal-set resin that are stable against environmental challenges consisting of hydrolysis, corrosion, enzymatic degradation, and bacterial challenges.

In an aspect, disclosed are new and non-obvious compositions of resin monomers that enhance the polymerization rate of styrene derivatives over that achievable with current compositions and associated methods by the addition of methacrylate (MA) derivatives, and photo-initiators. Furthermore, with the herein disclosed compositions and methods, the fractions of styrene derivative and MA derivatives in the monomer mixtures can be kept in the polymeric state, and these fractions can be maintained throughout the process of polymerization no matter how fast the polymerization is. Viscosity of monomers will not cause fraction drift in the polymer. Diffusion limitation of copolymerization is overcomed by using monomers containing carbamate functional groups.

In an embodiment, the novel and non-obvious composition of matter includes two or more vinyl-containing monomer(s); and one or more initiators, where the two or more vinyl-containing monomers undergo vinyl conversion to form a composition-controlled resin.

In an aspect, the two or more vinyl-containing monomer(s) are chosen from a group consisting of mixtures of methacrylate derivatives and styrene derivatives, and mixtures of acrylate derivatives and styrene derivatives; and the methacrylate and styrene moieties or the acrylate and styrene moieties are in a same monomer or different monomers.

In another aspect, one or more of the vinyl-containing monomer(s) have functional groups selected from a group consisting of one or more carbamate groups and/or derivatives; one or more urethane groups and/or derivatives; and one or more amine groups and/or derivatives.

In yet another aspect, the initiators are selected from a group consisting of photo-initiator(s) including camphorquinone or derivatives; a combination of camphorquinone or derivatives and amine(s), including ethyl-4-N, N-dimethylaminobenzonate; Phenylpropanedione or derivatives, including 1-phenyl-1,2-propanedione; and Bisacrylphosphine oxide or derivatives including bis(2,4,6-trimethylbenzoyl)-phenylphosphineoxide (Irgacure 819), bis(2,6-dimethoxy benzoyl)-trimethylpentyl phosphine oxide and 1-hydroxycyclohexyl phenyl ketone, wherein the photo-initiators may be used with/without diaryl iodonium derivatives, and with/without boryl radicals including tert-butylamine borane complex.

In still another aspect, the composition is used to achieve composition control of a forming polymer, wherein the mole fraction of acrylate/methacrylate moieties and styrene moieties in the forming polymer is determined preferably by the chemistry and composition of the feeding monomers rather than the viscosity of the feeding monomers.

DESCRIPTION OF THE DRAWINGS

The detailed description refers to the following Figures in which like numerals and symbols refer to like objects, and in which:

FIGS. 1A and 1B illustrate examples of methacrylate (MA) derivatives that may be added to a composition containing styrene derivatives for use in dental compositions;

FIG. 2 illustrates an example of a styrene derivative for use in dental compositions; and FIG. 3 illustrates a precursor composition for dental applications that provides azeotropic photo-copolymerization of the MA derivatives and styrene derivative of FIGS. 1A, 1B, and 2.

DETAILED DESCRIPTION

With current compositions and associated methods, photo-polymerization of styrene derivatives occurs too slowly to be practically useful in dental applications. Disclosed herein are precursor compositions (resin monomer compositions) that include styrene derivatives and that reach satisfactory vinyl conversion within a time frame that is suitable for dental applications such as, for example, dental preventive and restorative applications, laminate veneers, denture, denture repairing materials, inlays and onlays, fixed bridges, implants, resin reinforce cements, placement of ceramic restorations, and sealants. Also disclosed are methods for producing satisfactory resins for such dental applications.

With an ever-growing impetus to produce new, advanced functional materials, many synthetic approaches and conceptual designs have been developed, and opportunities are opened. A clinically implementable system that makes high performance functional polymeric materials on site, especially those with well-defined chemical structures, is appealing for various applications, including medical devices, coatings, packaging, electronic devices, and the automobile industry. Photo-polymerization also may be used as a photographic or printing process, because polymerization only occurs in regions that have been exposed, to light. Unreacted monomer can be removed from unexposed regions, leaving a relief polymeric image. Several forms of 3D printing—including layer-by-layer stereo lithography and two-photon absorption 3D photo-polymerization—also use may photo-copolymerization.

In an aspect, the precursor compositions include a styrene derivative to which is added a small amount of methacrylate (MA) derivatives. The methacrylate derivatives may contain urethane groups, carbamate groups, amide, and/or amine groups, preferably urethane groups as shown in FIGS. 1A and 1B, which illustrate two different forms of urethane dimethacrylate (UDMA). The UDMA may serve as a co-initiator in the herein disclosed photo-curable dental resins, and such UDMA containing resins should have a higher double bond conversion than would bisphenol A glycidyl dimethacrylate/triethylene glycol dimethacrylate (Bis-GMA/TEGDMA) resins. In addition, the UDMA containing copolymers should have a comparable or better mechanical performance (including fracture toughness and elastic modulus) than would current dental resins, such as, Bis-GMA/TEGDMA containing copolymers.

FIG. 2 illustrates an example styrene derivative that may be used with the methacrylate derivatives of FIGS. 1A and 18B. In particular, FIG. 2 illustrates triethyleneglycol divinylbenzyl ether (TEG-DVBE) with two styrene groups. However, other styrene derivatives may be used.

In another aspect, the precursor composition may be comprised of a fraction of methacrylate derivatives, up to 80 percent by weight (80 wt %), preferably 50 wt %. As can be seen in FIG. 3, the precursor composition also may include photo-initiators in addition to the above-mentioned UDMA. In an embodiment, the photo-initiators may include quinone and amine initiator systems such as combinations of camphorquinone and ethyl-4,N, N-dimethyl-aminobenzonate.

The precursor composition may be cured by light irradiation, and preferably by visible light. or by heating. The polymerization may occur after the precursor composition infiltrates into pores object, wherein the porous objects include mental oxide, ceramic, chitosan, polysaccharide particles, metal, and wood.

Finally, the above monomers may be mixed with or without solvents or with or without fillers such as silica particles, metal oxide particles, ceramic particles, chitosan, polysaccharide particles, and the particles are in nano-scale and micro-scale size.

By co-polymerizing with the methacrylate derivatives, the styrene derivatives may reach about a 60 percent or more vinyl conversion within about one minute of light irradiation.

Further, the copolymerization of the precursor composition follows an alternating copolymerization kinetics, and the precursor composition has an azeotropic composition at the equimolar of styrene and methacrylate derivatives. Azeotropic composition means the mole ratio of styrene and methacrylate in monomers is the same as that in the copolymer and is independent of the polymerization rate. This monomer reactivity controlled process depends on the monomer and initiator used in the system. As a consequence, the repeating unit of copolymers is styrene-alt-methacrylate, and the reactivity is controllable through the feeding monomers, particularly when equimolar styrene derivative monomers and methacrylate derivative monomers are used. By selective control of the chemical structure of the feeding monomers, the desired performance of the light-cured dental resin is achieved; in particular, the feeding monomers are controlled to produce a dental resin having the desired polymerization shrinkage, hydrophilicity, hydrophobicity, and hydrogen bonding.

Furthermore, the dental resin formed using the monomers of FIGS. 1A, 1B, and 2 represents an improvement over current dimethacrylate (DMA) dental resins, which contain hydrolyzable ester groups. These ester groups may be split by acids, bases, and esterase present in the oral environment, leading to a short service life and leaching of unreacted monomers, bisphenol A (BPA), and system degradation products. The new resin network at equimolar composition not only replaces 50% of the hydrolysable ester groups with hydrolytically stable ether-based monomers, it is formed with composition controlled polymers, which generate local heterogeneity due to the chemical structure difference between VBE and MA. The new resin network also may obstruct or limit big enzymes from contacting the ester groups through steric effects and thus prevent degradation of the ester groups. In addition, esterase enzymes from saliva and cariogenic bacteria have chemical selectivity to ester-based monomers; for example, acetylcholinesterase (CE) is more active on Bis-GMA, and pseudocholineesterase (PCE) is more active on TEGDMA, which may also be disturbed by the new chain structure (resin network) in the new compositions disclosed herein.

Still further, for MA derivatives containing urethane groups, carbamate groups, amide groups, and amine functional groups, preferable urethane groups serve an additional function as co-initiators, thereby reducing the amount of leachable photo-initiators needed in the precursor composition. Thus, the forming polymer is more biocompatible and safer for use in dental applications.

Finally, with the herein disclosed precursor compositions, viscosity does not cause a deviation in the co-polymer composition as may happen in DMA-based co-polymer compositions.

Following are examples of compositions and methods related to rapid azeotropic photo-copolymerization. In these examples, the commercial monomers UDMA and ethoxylated bisphenol dimethacrylate (EBPADMA) were supplied by Esstech (Essington, Pa., USA) and were used as received. TEG-DVBE was synthesized and fully characterized by the applicant. The resin formations in the examples were activated either by 0.2 wt % of camphorquinone (CQ, Aldrich, Saint Louis, Mo., USA) and 0.8 wt % of ethyl 4-N,N-dimethylaminobenzoate (amine, Aldrich, Saint Louis, Mo., USA) or Irgacure 1819 for visible light photo-polymerization.

EXAMPLE 1

This example involves the use of FTIR spectroscopy, real-time Raman micro-spectroscopy, and 1H NMR spectroscopy to evaluate the composition of monomer mixtures and their copolymers. The absorbance or scattering of vinyl groups on TEG-DVBE (a styrene-derivative) and UDMA (a methacrylate-derivative) were identified, separated, and quantified using FTIR spectroscopy and Raman spectroscopy. The vinyl groups on TEG-DVBE formed a stronger conjugation with their benzene rings than the vinyl groups on UDMA did with carboxyl groups. In addition, the di-substitution (methyl and carboxyl) of the β-carbon of methacrylates may cause the C=C stretching to shift to a lower energy. As a result, the vinyl groups on TEG-DVBE and UDMA exhibited peaks at approximately 1629 $cm^{-1}$ and 1638 $cm^{-1}$, respectively, in both FTIR and Raman spectra. The separation and quantification of the C=C peaks of these two monomers was realized through peak-fitting using mathematical models developed for FTIR and Raman. In the wave number ranging from 1580 $cm^{-1}$ and 1660 $cm^{-1}$, four peaks were identified. Besides the absorption of C=C stretching of vinyl groups, the C=C stretching of the benzene ring from TEG-DVBE (1612 $cm^{-1}$) and N—H bending from UDMA (1623 $cm^{-1}$) were observed, respectively.

EXAMPLE 2

The mixture of TEG-DVBE and UDMA monomers at an azeotropic composition (i.e., 1/1 mole ratio) had higher reactivity toward free-radical photo-polymerization than ethoxylated bisphenol A dimethacrylate (EBPADMA) and approximately the same reactivity as that of UDMA. For the degree of vinyl conversion (DC) of EBPADMA, UDMA and UDMA/TEG-DVBE mixtures immediately after light irradiation (20 seconds, 40 seconds, or 60 seconds, using Smartlite® Max at 1600 mW/$cm^2$), mixtures of CQ and 4E (0.2 wt % and 0.8 wt %, respectively) were used as initiator. Using the same initiators and curing light, the DC of monomer mixtures (UDMA/TEG-DVBE/=1/3) reached 79% immediately after 40 seconds of light irradiation. Increasing the amount of UDMA will makes the polymerization rate even faster. At a 1/1 mole ratio, UDMA/TEG-DVBE Initiated by CQ/4E was found to be the fastest system among the three systems evaluated with different initiators and monomer mixtures.

EXAMPLE 3

As noted herein, and as described in this example 3, azeotropic composition in copolymers means that the fractions (mole ratio) of the starting monomers are the same as their fractions in the copolymers, and this mole ratio is constant throughout the copolymerization. As an example, alternating copolymers of styrene and methylmethacrylate have an azeotropic composition, 1/1 by mole. Three methods, FTIR-ATR, confocal Raman micro-spectroscopy, and NMR were used to confirm that equimolar UDMA/TEG-DVBE was an azeotropic composition when CQ/4E was used as an initiator, but not when Irgacure 819 was used as an initiator. The vinyl groups on TEG-DVBE (peak at 1630 $cm^{-1}$) and UDMA (peak at 1639 $cm^{-1}$) were identified and separated by both FTIR and Raman, and the intensity ratio of these peaks was proportional to the mole ratio of the corresponding two monomers. Kinetic studies using confocal Raman micro-spectroscopy confirmed that the ratio of peak intensity of UDMA/TEG-DVBE did not change, no matter how fast the photo-copolymerization was, and how high the DC was. The polymerization rate was controlled through the intensity of irradiation light to obtain fast (150 mW/$cm^2$ for 20 seconds) and slow (4 mW/$cm^2$ for 5 seconds) reaction. In addition, NMR also confirmed that the mole ratio of monomers was constant (1/1) at different DCs, from 5% to 60%. Using the same NMR method, UDMA (viscosity 7000 cP) was found to have a reduced fraction at high DC in copolymers with TEGDMA, due to viscosity effects. Even TEG-DVBE had the same low viscosity (29 cP) as TEGDMA (12 cP), applicant did not observe any viscosity effects throughout all of the reaction conditions that were evaluated.

EXAMPLE 4

Diffusion limitations lead to less monomer conversion (lower DC) of high viscosity monomers when no carbamate functional groups are in the monomers. The copolymerization of mixture of EBPADMA with TEG-DVBE, 1/1 by mole, initiated by camphor quinone and Amine showed that more TEG-DVBE was converted into polymer, and the mole fraction of TEG-DVBE-polymer is higher than polymerized EBPADMA at high monomer conversion. The mixture of monomer and initiators was irradiated for 20 seconds with a curing gun at 400 mW/$cm^2$. The DC of each monomer during copolymerization was monitored by real-time FTIR.

EXAMPLE 5

Diffusion limitations lead to less monomer conversion of high viscosity monomers when no carbamate functional groups are in the monomer. The copolymerization of mixture of EBPADMA with TEG-DVBE, 1/1 by mole, initiated by 1819 showed that more TEG-DVBE was converted into polymer, and the mole fraction of TEG-DVBE-polymer was higher than polymerized EBPADMA at a high monomer conversion. The mixture of monomer and initiators was irradiated for 20 seconds with a curing gun at 400 mW/$cm^2$. The DC of each monomer during copolymerization was monitored by real-time FTIR.

EXAMPLE 6

Diffusion limitations lead to more monomer conversion of high viscosity monomer when carbamate functional groups are in the high viscosity monomer. The copolymerization of a mixture of UDMA with TEG-DVBE, 1/1 by mole, initiated by 1819 showed that more UDMA was converted into polymer, and the mole fraction of UDMA-polymer is higher than polymerized TEGDVBE at high monomer conversion. The mixture of monomer and initiators were irradiated for 20 seconds with a curing gun at 400 mW/$cm^2$.

EXAMPLE 7

The copolymer of UDMA/TEG-DVBE generated less stress than the Bis-GMA/TEGDMA at the same DC when initiated by CQ/amine.

EXAMPLE 8

A composite was made by resin (25% by mass) and silica particles as fillers (75% by mass). The resin was a mixture of UDMA/TEG-DVBE 3/1 (by mole) and CQ/4E. The mixture was cured by light irradiation, and the cured composite had the same rigidity as composites made of Bis-GMA/TEGDMA but had significantly high flexural strength and toughness.

EXAMPLE 9

The degree of vinyl conversion (DC) of the mixture of UDMA/TEG-DVBE (1/1 by mole) with CQ/amine as initiator was approximately 86% after 1 min of light irradiation. The DC was further increase by heat. The DC was approximately 96% after 24 hours at 60 degrees centigrade; and the DC reached >99% after 0.5 hours at 200 degrees centigrade.

EXAMPLE 10

This example describes photo-polymerization methods. Monomer mixtures were sandwiched between two Mylar films (10 µL, for FTIR-ATR measurement) or sealed in capillary glass tubes (Vitrocom, Mt. Lks. N.J., USA; 0.40× 4.0 I.D., for real-time Raman micro-spectroscopy evaluation) and photo-cured using a handheld dental curing light (SmartLite max LED curing light, model: 644050, Dentsply International, Milford, Del., USA). The intensity of light irradiation was adjusted through the distance of light to samples.

EXAMPLE 11

This example determined DC using FTIR-ATR and peak fitting methods: Degree of conversion (DC) was evaluated immediately after curing using a Thermo Nicolet Nexus 670 FT-IR spectrometer (Thermo Scientific, Madison, Wis., USA) with a KBr beamsplitter, an MCT/A detector and an attenuated total reflectance (ATR) accessory. The areas of absorption peaks of the vinyl group of TEG-DVBE at 1629 $cm^{-1}$, and the methacrylate groups of UDMA at 1638 $cm^{-1}$ were integrated, and the DC was calculated using the aromatic group of TEG-DVBE at 1612 $cm^{-1}$ or the amide group of UDMA at 1537 $cm^{-1}$ as an internal standard. Peaks were resolved with the assistance of the curve fitting program Fityk (version 0.9.8). In order to correct potential discrepancies, a standard curve was produced by plotting varied resin composition ratio values analysed by NMR spectroscopy against the values obtained through FTIR peak fitting. The phenyl absorbance at 1612 $cm^{-1}$ was the internal standard for TEG-DVBE homo-polymers. DC was calculated according to the following equation: DC=(A1/A0−A1'/A0')/(A1/A0) 100%, where A1/A0 and A1'/A0' stand for the peak-area-ratio of vinyl-of-interest and internal standard before and after polymerization, respectively. The vinyl-of-interest may be vinyl groups from TEG-DVBE, UDMA, or both.

EXAMPLE 12

Sol-gel experiment: Resin specimens were placed in a stainless steel mold (13 mm in diameter and 1 mm in thickness) and then cured for different time scales (10 seconds, 20 seconds and 60 seconds) with a Triad 2000 visible light curing unit (Dentsply, York, Pa., USA) fitted with a tungsten halogen light bulb (75 W and 120 V, 43 mW/$cm^2$). The samples were then weighed and their DCs were determined by FITR-ATR immediately after the curing. In a pre-weighed vial, each sample was extracted twice using 5 mL deuterated methylene chloride (CDCl3) containing 0.01 wt % butylated hydroxytoluene (Aldrich, Saint Louis, Mo., USA) via continuous shaking for 48 hours. The solution (sol) fractions from these two extractions were combined and concentrated via rotary evaporation under reduced pressure until no further changes in weight were observed. 1H NMR (Bruker 600 MHz) was conducted for each sol fraction sample to determine the monomer ratio. The remaining gel fraction was collected and dried via in-house vacuum to yield a constant weight, and the DC was measured by FTIR-ATR.

EXAMPLE 13

Real-time Raman micro-spectroscopy: method description, peak fitting method, and real-time DC evaluation. Raman spectra were acquired from dried residues using a Renishaw S1000 micro-Raman spectrometer (Renishaw, Gloucestershire, UK) consisting of a Leica DMLM microscope coupled to a 250 mm focal length imaging spectrograph with a proprietary deep depletion, thermoelectrically cooled (70 degrees centigrade) charge-coupled device. For this work, a 632.8 nm helium-neon laser (Model 1144P, JDS Uniphase, Milpitas, Calif.), holographically ruled 1800 grooves $mm^{-1}$ grating, and 20× objective (Leica N PLAN) were used. The excitation laser was focused to a line approximately 50 µm long at the sample position and aligned to the spectrograph entrance slit to maximize throughput. The line focus was utilized to reduce laser power density at the sample. Laser power measured at the sample position was approximately 12 mW. Depending on the desired spectral range, data was acquired using a static grating position covering the Raman shift range from 1275 $cm^{-1}$ to 1790 $cm^{-1}$ (577 data points) or a grating step scan mode covering the Raman shift range from 500 cm-1 to 1800 cm-1 (1369 data points). Integrations time was typically 1 s/pixel. Spectral resolution was approximately 3 $cm^{-1}$. To further minimize any unintended impacts of laser illumination on the photo-polymerization the samples used in the kinetic studies were slowly translated laterally throughout data acquisition. This was done using the motorized microscope translation stage and Raman mapping capabilities in the spectrometer control software (WiRE 3.1, Renishaw, Gloucestershire, UK).

Estimation of the degree of conversion of the monomers was accomplished using a direct classical least squares (CLS) multivariate regression approach. Pure spectra of each monomer were acquired by placing the neat materials in the same vessels as used for the photo-polymerization kinetic studies and collecting spectra with equivalent excitation laser power and integration time to provide spectra that were quantitative relative to one another. The spectral range was restricted to a narrow spectral range from 1625 $cm^{-1}$ to 1660 $cm^{-1}$, which corresponds to the stretching modes of the terminal vinyl groups on each monomer. This narrow range was necessary because of band intensity changes and small band shifts observed for many of the vibrational modes as a consequence of the polymerization. Blending of the monomers appeared to introduce small peak shifts (≤0.5 $cm^{-1}$) in the vinyl stretching modes that were correlated with the mixture composition. The pure spectra were shifted slightly prior to application of the CLS method in order to minimize the fit residuals. In addition to the two monomer pure spectra, a constant offset was fit in the CLS model in order to correct for baseline variations that arose during the experiments. A simple constant was deemed adequate because the CLS models were fit over a very narrow region of 35 cm-1, which corresponds to a spectral band of only 1.75 nm, and fluorescent background interferences generally have much broader spectral profiles. The CLS scores are the contribution of each component of a linear combination of the pure spectrum in a least squares fit of the sample spectra. This is essentially a rigid peak fitting using an arbitrary experimentally measured peak function with a single parameter that corresponds to intensity. The pure spectra were acquired under identical instrumental conditions and thus the CLS scores were assumed to correspond directly to the relative composition of the monomer mixture before and during the polymerization. To estimate degree of conversion of each monomer, the CLS scores for each polymerization data set were normalized by the average score for the given component from an initial data set (typically ten or more spectra) acquired prior to photo initiation.

EXAMPLE 14

Rapid Photo-polymerization: One of the synergetic effects of the model monomers is the significant improvement of polymerization rate of the styrene-derivative, TEG-DVBE, by adding UDMA. Free radical homo-polymerization of styrene is relatively slow in comparison with methacrylate, due to stabilization of free radicals through resonance with styrene's benzene ring. Without modifying the chemical structure of the monomer or inventing new initiators, copolymerization is one of the most efficient ways to accelerate polymer chain propagation because the rate of copolymerization is strongly affected by the competition of monomer reactivity ratios (r1 and r2), which overcomes the drawback of free-radical stabilization in homo-polymerization of TEG-DVBE. Although substantial work has been done to improve the polymerization rate of styrenic monomer in vinyl ester resins (VERs), (Rey et al. Macromolecules 2000, 33, 6780, and Scott et al. Macromolecules 2003, 36, 6066), the polymerization rate and low degree of vinyl conversion are still limiting factors for VERs to be used clinically in dental adhesives and dental composites. This experiment demonstrates the viability of using model monomers in dental clinics by reaching DC above 70% with 20 seconds of light irradiation. The DCs of TEG-DVBE, UDMA, and the equimolar mixture of TEG-DVBE and UDMA immediately after light irradiation (light intensity at 1600 mW/cm$^2$) for 20 seconds, 40 seconds, and 60 seconds were determined. The resulting low DC indicates that camphorquinone/ethyl 4-N,N-dimethylaminobenzoate (CQ/amine) are not efficient initiators for TEG-DVBE homo-polymerization. This initiator combination is however very effective on UDMA homo-polymer and the copolymer: their DCs reaching approximately 90% in 20 seconds.

EXAMPLE 15

Another noteworthy feature is the azeotropic composition at equimolar TEG-DVBE and UDMA when CQ/amine are used as initiators. Azeotropic compositions in copolymers mean that the mole fractions of the feed monomers are retained in the polymer and are constant throughout the polymerization process. FTIR also revealed that the DC of TEG-DVBE and UDMA in the above equimolar copolymers was the same, approximately 90%. The composition of copolymers was further evaluated by the sol-gel experiment. To extract enough leachable materials, the light intensity was reduced to mW/cm$^2$, and low DC copolymers were obtained. The progress of photo-polymerization was controlled by varying the time of light irradiation. Based on the peak-area analysis of the absorbance of C═C stretching in FTIR spectra and integration of 1H NMR signals associated with protons on C═C, the styrene-vinyl groups and methacrylate-vinyl groups had the same mole fraction in both gels and solubles. This suggests that the equimolar composition of the feed monomers was kept in these three polymerization stages from DC=5% to DC=62%.

EXAMPLE 16

The azeotropic composition confirmed by real-time Raman spectroscopy: Real-time Raman micro-spectroscopy further confirmed that the equimolar composition was constant over time during photo-polymerization and was independent of the polymerization rate, which was controlled through light intensity and irradiation time. To achieve a step-wise polymerization, specimens were exposed to light at 4 mW/cm$^2$ for 5 seconds up to a total of four exposures. The multivariate CLS method standardized using pure monomer spectra was used to estimate unpolymerized monomer composition in the samples using the C═C stretching bands of TEG-DVBE and UDMA. CLS scores for each specimen were normalized to 100 for the pre-polymerized monomer mixtures. As the vinyl groups converted to polymers, the associated C═C band intensity decreased, and the DC increased accordingly. At each light irradiation, the intensity dropped immediately, which was followed by further decrease at a much slower rate, until the next irradiation. During the full time range (10 minutes) of this set of experiments, DC reached approximately 20%, and the mole ratio of TEG-DVBE/UDMA remained 1/1. A faster photo-polymerization took place when the sample was irradiated at 150 mW/cm$^2$ for 20 seconds. The DC of this specimen achieved approximately 55% immediately after light irradiation; after 1 hour, the DC was approximately 65%; after 1 day, it was approximately 72%. During the course of this set of experiments, the mole ratio of TEG-DVBE and UDMA was always 1/1.

EXAMPLE 17

The azeotropic composition predicted by monomer reactivity ratios: Monomer reactivity ratios were evaluated to understand the kinetics behind the azeotropic composition at equimolar composition. The polymer composition (F) was determined by Raman micro-spectroscopy according to the CLS score ratios of TEG-DVBE and UDMA at low DCs (1-3%). A classic instantaneous copolymerization equation for non-cross-linking polymers was used to compare F with the monomer feed composition (f, mole fraction) based on an assumption that at such low DCs, the two vinyl groups in one molecule act independently without interfering with each other.

The feed ratios of monomers may not always determine the compositions of the final material. Feeds with a molar ratio UDMA/TEG-DVBE>0.5 are expected to produce networks depleted in their UDMA content relative to the feeds, and UDMA/TEG-DVBE<0.5 produce networks enriched in UDMA. The composition data were fit to an equation with a nonlinear least-squares (NLLS) optimization after van Herk. The monomer reactivity ratios, rUDMA and rTEGD-VBE, are 0.64±0.11 and 0.55±0.12, respectively. They are slightly, but statistically significantly, higher than the reactivity ratios of styrene and methyl methacrylate, r1≈r2≈0.5. These reactivity ratios suggest a polymerization mechanism somewhat biased towards cross-propagation and alternating sequences, characteristic of styrenic-methacrylic copolymer systems.

EXAMPLE 18

The effects of viscosity and monomer chemistry on composition control: Both of the sol-gel experiments and kinetic studies suggest the copolymerization of TEG-DVBE and UDMA is a monomer-chemistry-controlled process. The viscosity of monomer shows no consequential role during the polymer chain propagation, considering that the viscosity of UDMA (6.631±0.100 Pa·s) is approximately 240 time higher than that of TEG-DVBE (0.029±0.001 Pa·s). In contrast, copolymerization of UDMA and triethylene glycol dimethacrylate (viscosity=0.050 Pa·s) showed significantly composition drift when DC was above 20% because the low viscosity monomers diffused faster in resin networks than the base monomers and reached the propagating chain quicker, thus more of them were converted into polymers at high DCs. Although the exact mechanism that leads to such rapid photo-polymerization and well-controlled azeotropic composition is yet to be defined, UDMA has dual roles: monomer and co-initiator when initiated by CQ/amine. The carbamate functional group in UDMA may form a free radical on a methylene group adjacent to its N—H groups. This may be achieved via electron transfer from the light-excited CQ. Experimentally, the photo-polymerization rate of UDMA initiated by CQ alone was similar to that by CQ/amine, and the photo-bleaching rate of CQ in UDMA also showed minimal differences with/without amine.

I claim:

1. A composition of matter, comprising:
    two or more vinyl-containing monomers consisting of at least two different types of vinyl functional monomers, wherein the two or more vinyl-containing monomers are triethyleneglycol divinylbenzyl ether (TEG-DVBE) and methacrylate derivatives; and
    one or more initiators;
    wherein the two or more vinyl-containing monomers undergo vinyl conversion to form a composition-controlled cross-linked resin.
2. The composition of matter of claim 1, wherein the methacrylate derivatives have functional groups selected from a group consisting of:
    one or more carbamate groups and/or derivatives;
    one or more urethane groups and/or derivatives; and
    one or more amine groups and/or derivatives.
3. The composition of matter of claim 1, wherein the one or more initiators are selected from a group consisting of:
    photoinitiator(s) comprising camphorquinone or derivatives,
    a combination of cam phorquinone and amine(s) derivatives, phenylpropanedione or derivatives, bisacylphosphine oxide or derivatives, or 1-hydroxycyclohexyl phenyl ketone,
    wherein the initiators may be used:
    with/without diary iodonium derivatives, and
    with/without boryl radicals.
4. The composition of matter in claim 1, wherein a mole fraction of methacrylate derivatives and TEG-DVBE moieties in the composition-controlled cross-linked resin is determined by the mole fraction corresponding to the methacrylate derivatives and TEG-DVBE.
5. The composition of matter of claim 1, wherein the composition is used as dental materials that are used with or without fillers as restorative materials, laminate veneers, denture, denture repairing materials, dental adhesives, resin reinforce cements, placement of ceramic restorations, and sealants.
6. The composition of matter of claim 1, wherein the composition is used in 3D printing.
7. The composition of matter of claim 1, wherein the composition controlled cross-linked resin is stable against environmental challenges consisting of hydrolysis, corrosion, enzymatic degradation, and bacterial challenges.
8. The composition of matter of claim 1, wherein the composition is used to make polymers as packaging materials, coating materials and adhesives.
9. The composition of matter of claim 1, wherein the composition is used to make composition-controlled polymers with alternating methacrylate derivatuves/TEG-DVBE moieties in the chain of the polymers.
10. A composition of matter made by polymerizing the composition of claim 1 with or without fillers using methods comprising of light irradiation and/or heating.
11. The composition of matter of claim 10, wherein the fillers are selected from a group consisting of:
    metal oxide particles, ceramic particles, chitosan, polysaccharide particles, and
    the particles are in nano-scale and micro-scale.
12. The composition of matter of claim 10, wherein the composition is used as dental materials, restorative materials, laminate veneers, denture, denture repairing materials, dental adhesives, inlays and onlays, fixed bridges, implants, resin reinforce cements, placement of ceramic restorations, and sealants.
13. A composition of matter made by polymerizing the composition of claim 1 after the composition infiltrates into pores of porous objects using methods comprising of light irradiation and/or heating.
14. The composition of matter of claim 13, wherein the porous objects are selected from a group consisting of:
    metal oxide, ceramic, chitosan, polysaccharide particles, metal, and wood.
15. The composition of matter of claim 13, wherein the composition is used as dental materials, restorative materials, laminate veneers, denture, denture repairing materials, dental adhesives, inlays and onlays, fixed bridges, implants, resin reinforce cements, placement of ceramic restorations, and sealants.
16. A composition of matter made by polymerizing the composition of claim 1 to make vinyl-free polymers, polymers with no polymerizable vinyl groups, using methods comprising light irradiation and/or heating.
17. The composition of matter of claim 16, wherein the composition is used independently or as a component in medical devices, electronic devices, and solar cells.
18. The composition of matter of claim 1, wherein a copolymer of methacrylate derivatives and TEG-DVBE generates less stress than a bisphenol A glycidyl methacrylate/triethylene glycol dimethacrylate (BisGMA/TEGDMA) copolymer at the same degree of vinyl conversion when initiated by a combination of camphorquinone and amine.

* * * * *

UNITED STATES PATENT AND TRADEMARK OFFICE
CERTIFICATE OF CORRECTION

Page 1 of 1

PATENT NO. : 10,246,540 B2
APPLICATION NO. : 15/276821
DATED : April 2, 2019
INVENTOR(S) : Jirun Sun It is certified that error appears in the above-identified patent and that said Letters Patent is hereby corrected as shown below:

In the Specification

The following should appear in Column 1, following the paragraph at Lines 6 - 14:
STATEMENT OF FEDERALLY SPONSORED RESEARCH
This invention was made with government support under grant U01 DE023752 awarded by the National Institutes of Health. The government has certain rights in the invention.

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*